(12) United States Patent
Froloff

(10) Patent No.: US 11,335,454 B2
(45) Date of Patent: May 17, 2022

(54) BIOPSY DEVICE FOR DIGITAL PATHOLOGY AND ARTIFICIAL INTELLIGENT ANALYTICS

(71) Applicant: Walt Froloff, Aptos, CA (US)

(72) Inventor: Walt Froloff, Aptos, CA (US)

(*) Notice: Subject to any disclaimer, the term of this patent is extended or adjusted under 35 U.S.C. 154(b) by 0 days.

(21) Appl. No.: 16/427,002

(22) Filed: May 30, 2019

(65) Prior Publication Data
US 2020/0381103 A1  Dec. 3, 2020

(51) Int. Cl.
| | | |
|---|---|---|
| *G16H 30/40* | (2018.01) | |
| *G16H 50/20* | (2018.01) | |
| *G16H 80/00* | (2018.01) | |
| *A61B 10/02* | (2006.01) | |
| *A61B 5/00* | (2006.01) | |
| A61B 1/07 | (2006.01) | |
| G02B 21/36 | (2006.01) | |
| G02B 21/00 | (2006.01) | |

(52) U.S. Cl.
CPC ........... *G16H 30/40* (2018.01); *A61B 5/0071* (2013.01); *A61B 5/444* (2013.01); *A61B 10/0233* (2013.01); *G16H 50/20* (2018.01); *G16H 80/00* (2018.01); *A61B 1/07* (2013.01); *A61B 5/0064* (2013.01); *A61B 5/0075* (2013.01); *G02B 21/002* (2013.01); *G02B 21/367* (2013.01)

(58) Field of Classification Search
CPC ........ G16H 30/40; G16H 50/20; G16H 80/00; A61B 5/0071; A61B 5/444; A61B 10/0233; A61B 1/07; A61B 5/0064; A61B 5/0075; G02B 21/002; G02B 21/367
See application file for complete search history.

(56) References Cited

U.S. PATENT DOCUMENTS

| | | | | |
|---|---|---|---|---|
| 2010/0249506 A1* | 9/2010 | Prisco | ................ | A61B 1/00059 600/117 |
| 2013/0148196 A1* | 6/2013 | Arnold | ..................... | G02F 1/11 359/385 |

(Continued)

OTHER PUBLICATIONS

Wikipedia, Penetration depth [downloaded Oct. 22, 2021], 2021 < https://en.wikipedia.org/wiki/Penetration_depth > (3 pages) (Year: 2021).*

*Primary Examiner* — David F Dunphy
(74) *Attorney, Agent, or Firm* — Walt Froloff

(57) ABSTRACT

An in vivo of insitu bio-matter sample magnified digital image creating device for realtime biopsy determinations having a sharp edged window pocket coupled to housing having an optical and digital magnification path coupled to image detecting sensor logic. The device has an optical two blade window pocket rotatably coupled to a stem mechanically controlled and extendable from mechanism within the housing, the stem having source for at least one fiber optical channel for selected frequency and wavelength light various light sources, an optical two blade window pocket slide component optically coupled to the two blade window pocket fiber optic channel stem distal end, providing light through the two blade window pocket slide normal axis surface for illumination penetrating a bio matter assay or sample for imaging through an optical microscopy magnification path axis to a micrograph image sensor. The resulting image micrographs for digital pathology realtime result determination.

20 Claims, 12 Drawing Sheets

(56) References Cited

U.S. PATENT DOCUMENTS

2015/0057553 A1\* 2/2015 Shumate .............. A61B 5/0071
                                              600/478
2016/0367148 A1\* 12/2016 Froloff ............... A61B 1/00009
2020/0100777 A1\* 4/2020 Mohanty .............. A61B 1/0684

\* cited by examiner

BIOPSY DEVICE FOR DIGITAL PATHOLOGY AND ARTIFICIAL INTELLIGENT ANALYTICS

BACKGROUND

Field of the Invention

The present invention relates generally to the field of biopsy pathological analysis and specifically to digital pathological and artificial intelligence analytics for realtime or near realtime biopsy analytics.

Background Description

Pathology lab analysis from physical biopsies remain the gold standard, with human pathologists using microscopes to diagnose disease and infection by assessing physical tissue biopsy assays fixed on physical glass slides. Pathology is potentially the most powerful field of medicine. It is often the first place for definitively diagnosing a disease. As a consequence, a vast majority of decisions made with regards to patient care—up to 80 percent—are influenced by pathology. Unfortunately for the same reason, it's also potentially the largest contributor to the $750 billion problem of misdiagnoses facing the health care system in the US.

Moreover, the logistics involved from obtaining a biopsy from the patient to doctor to pathologist slide preparation and analysis, back to doctor and then back to patient instill a whole new set of problems that only add to time, cost and patient waiting, anguish and physical suffering.

Skin Cancer

More than a million people in the US each year a find a strange looking spot or scabby looking irregularly shaped, dark brownish mole, or irregular legion, maybe a darkish color changing scabby texture spot or bump, somewhere their your body. This anomalous skin growth can be a skin cancer or a precursor. It's totally curable if caught in time. Approximately 30,000 people in the US die every year from melanoma, carcinoma or other type of skin cancer because they for whatever reason did not get the anomaly checked out. What is needed is an easier way to check for skin cancer, where the doctors visit and pathological exam did not occur and where time, logistics and or cost are life threatening.

Slide Scanner Technology

With the rise in whole slide scanner technology, large numbers of tissue slides are being scanned and represented and archived digitally. While digital pathology has substantial implications for telepathology, second opinions, and education there are also huge research opportunities in image computing with this new source of "big data". It is well known that there is fundamental prognostic data embedded in pathology images. The ability to mine "subvisual" image features from digital pathology slide images, features that may not be visually discernible by a pathologist, offers the opportunity for better quantitative modeling of disease appearance and hence possibly improved prediction of disease aggressiveness and patient outcome.

Developments in computational image analysis tools for predictive modeling of digital pathology images from a detection, segmentation, feature extraction, and tissue classification perspective are emerging with ever new feature approaches, with improved predictive modeling of tissue appearance and deep learning schemes for both object detection and tissue classification. What is needed are technological bridges to provide the transfer of images from the physical in vivo to the digital.

In the United States, a vaginal biopsy test itself costs $20 to $30, but the costs for doctor test visits can cost over $1,000, largely because additional tests are added that may or may not be necessary, depending on the pathology lab results. Results on occasion find a virus, a DNA virus which establish productive infections only in mucous membranes. Many HPV infections are subclinical and will cause no physical symptoms; however, in some people infections may cause benign squamous cell papilloma, or cancers of the cervix, vulva, vagina and other organs with mucous membranes. Out of the over a hundred variants. HPV16 and HPV18 are known to cause around 70% of cervical cancer cases. Surgical removal, topical creams and laser are the three methods currently used to excise these cancer agents. But biopsys are the best and most used method for early detection of suspect tissue, followed by treatment if an HPV precancerous squamous cell is found. What is needed are biopsy results that give a woman all the results all at one time, so that follow-on procedures can be established with out undue time and cost escalation. The same goes for skin cancers, whether squamous cell, basal cell, carcinoma, or melanoma.

Recent advancements in photonic microscopy diagnostics, detection and imaging technologies have made inroads into computer image processing and automation. Theses are emerging technologies which can replace outdated medical diagnostic and treatment processes. Many medical procedures are time consuming, logistically challenging for medical staff and doctors driving up medical and health care costs. In addition many ailments and maladies can be diagnosed, identified and remedied, using similar tools, techniques and procedures. Technology used in analyzing tissue, assay and blood samples in the medical arena are growing, but they are not well integrated. Technology fiber optics and photonics, endoscopes and microscopes, instruments used to examine the interior cavity of the body or organ and other process require the obtaining of samples manually, physical examination of samples at laboratories for manual inspection by a specialist. Much of this labor can be integrated through digital imaging, software, optical microscopy, LED and laser technology.

Photonics and Microscopy

Digital and optical microscopy have also seen tremendous inroads in the medical fields. However a multidisciplinary approach involving the collaboration between clinicians and technology developers is necessary for the implementation of new medical devices. Change and adoption are faster when the antiquated manual process methods prove too expensive on patients as well as medical and health care staff. What is needed are ways to obtain and analyze bio-samples more quickly using faster developed technology programmatically.

Digital Pathology

Healthcare costs are rising faster than people can pay them. An automated process for biopsies is needed to reduce costs. Counter to this trend, since 2015, Machine Learning AIs have out performed human experts on detection and identification for a given label in an image in many fields including medical from MRI, X-rays, Ultrasound, PET, CAT and others. What is needed is a way to image the physical tissue insitu or locally.

The digitization of tissue glass slides is opening up opportunities in computational imaging technology. Computational imaging will play a role in better quantitative characterization of disease and precision medicine. What is needed is a faster bridge from the physical to the digital to spur these developments. What are needed are machine automation for pathological analysis as waiting for humans to perform labor intensive lab tasks better done by computers is better faster and cheaper.

Platforms for better screening tools are needed to reduce the workload of technicians in high volume laboratories and the number of samples that require testing with Xpert and/or mycobacterial culture. Digital imaging also enables other strategies to improve accuracy and reduce workload. What is needed are AI analytics to rescue pathology labs, pathology lab technicians from slide making manual tasks better done by device.

SUMMARY

The present invention discloses an insitu bio-matter magnification device for digital analytics starting with a housing having an optical and digital magnification path coupled to image detecting sensor and logic, a sharp edged window pocket structurally coupled to a stem, window pocket component having an open enclosure with cutting edges for collecting bio sample. The window pocket provides photonic illumination source from a side of the collected sample and into the optical and digital magnification path, and the stem has at least one fiber optic channel for conducting selected pulsed or streamed frequency and wavelength light from single wavelength or tunable wavelength light sources into the window pocket. Also the window pocket component optically coupled an electro/optic channel stem distal end, for conducting selected frequency light from the housing to a window pocket side normal axis surface for illumination penetrating a specimen sample in the window pocket for optical imaging into an optical microscopy magnification path axis, with an optical microscopy magnification path magnifying and focusing images on a digital CCD or CMOS detector. The image detector is electronically coupled to electronic imaging logic for processing and display of micrograph images, moreover having logic for digital control, image focus and image processing of images responsive to the stem and optical path positioning for display of image processing results locally or wireless transfer to remote digital display device, whereby image comparisons and analytics can be accomplished and resulting digital image micrographs from optical two blade window pocket collection programmatically processed, identified and verified in situ in real-time.

In another embodiment of the invention the window pocket is an optical two cutting edge slab component forming a sample collecting enclosure coupled to an optical or electrical channel coupled stem coupled to a housing, stem rotatable and extensable-retractable under digital logic control.

BRIEF DESCRIPTION OF DRAWINGS

Specific embodiments of the invention will be described in detail with reference to the following figures.

DETAILED DESCRIPTION

Figure 1:
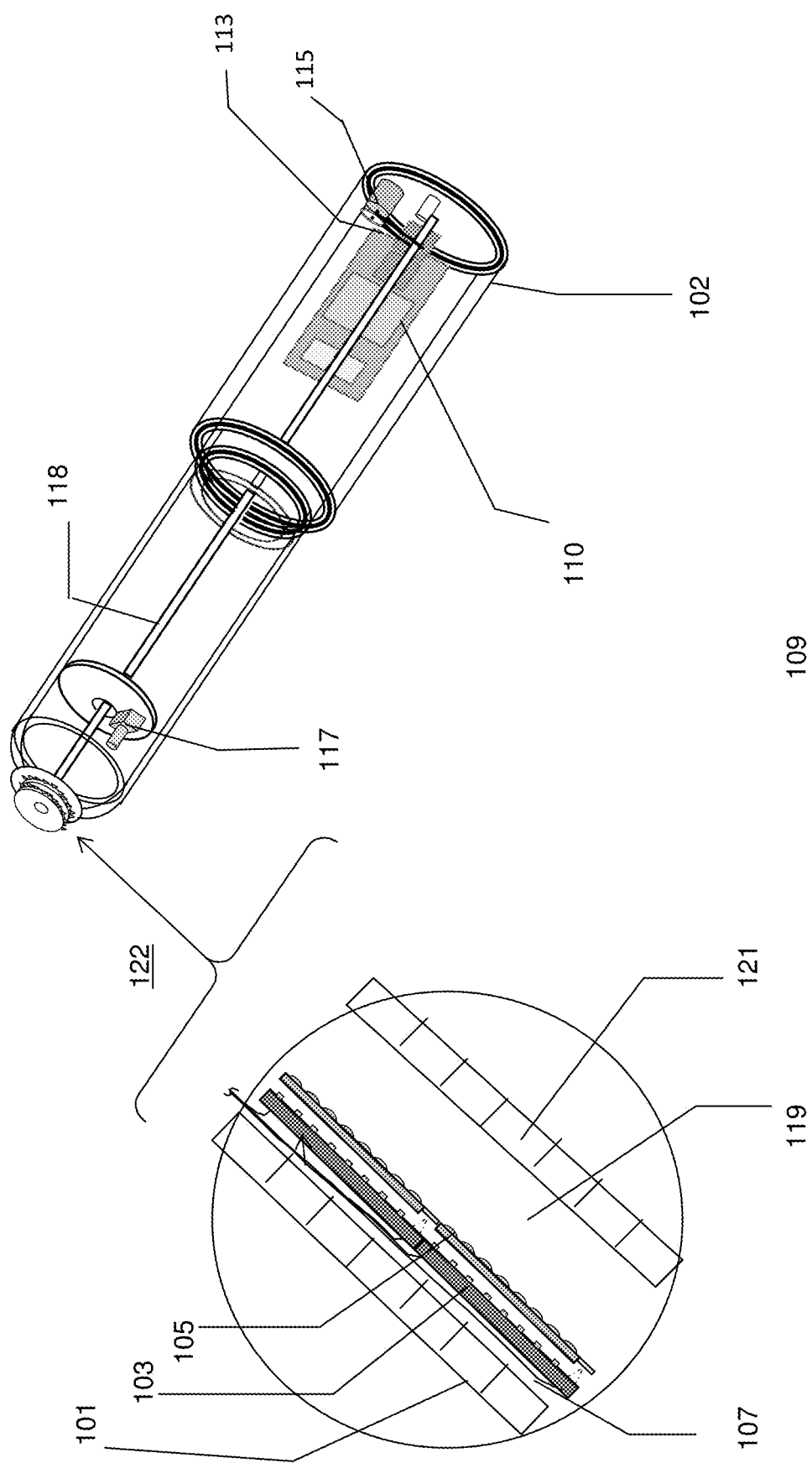
FIG. 1 is a cross sectional view of a biopsy micrograph scanning device tool in accordance with an embodiment of the present invention.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Objects and Advantages

An object of the invention is to design a way to obtain an in-vitro biopic micrograph from physical tissue for a pathological detection and identification by and a digital pathology AI analytic.

Another object if the invention is to create biopsy tissue slides in vitro for a micrographic image for high magnification digital pathological processing.

Yet another object of the invention is to reduce cost, labor and lab result delivery time from a medical biopsy device delivering in-vitro micrograph images directly to an AI for detection, identification and realtime response to doctor/patient.

Another object of the invention is to automate the diagnosis of biopsy biomatter from taking of the biopsy to identification and medical prognosis of the potential harm.

Yet another object of the invention is to automate the process from biopsy to remedial action.

Yet another object of the invention is to create tissue micrograph or photomicrograph image baselines for patients so that image comparisons can be made from historical data if existing or cloud for general image processing and Electronic Medical Record, EMR, facilitation.

Yet another object of the invention is to use medical image technology for insitu exams processing live micrograph image data with stored digital images for online or offline realtime diagnoses by AI analytics.

Embodiments of the Invention

Digital pathology analytics, not unlike many sampling methods, requires some bio-matter or sample to be removed from a patience by extracting tissues from a patient, or surgical removal for placement on a glass slide for biopic and or microscopic evaluation. Automated image processing of sample slides exist from the more typical expert medical lab examiner. An aspect of the invention provides a double blade circular cutting window biopsy tool which moves a layer tissue into an optical pocket equivalent to a slide sample, complete with backlighting for an automated digital image creation. The optical pocket is integrated with the components necessary for directing the wavelength or frequency light required at the timed trigger and image resolving durations for image magnifications as provided in lab slide sample analysis. The cutting and removing component is integrated with the photonic components such as mirrors, beam splitters, fractionalized phase plates, laser/light fiber conduit channels, etalons, in-plane lasers or edge-emitting lasers which emit from surfaces, vertical cavity surface emission laser, VCSEL, and other photonic and digital components into a semi-rigid structure which can be inserted and selectively positioned so as to collect images from a sample in an optical pocket for obtaining in vivo magnified images without having to create external and extrinsic slide samples for image analysis or evaluation outside the cavity and with resulting delays in results.

The cutting or slicing component support stem carries optical fiber and or power which functions as a conductor or waveguide, or "light pipe". to transmit power between the cutting window slide component optical flat plat surface and light source. The light source can be from a variety of sources as needed coming from LED, laser, tunable laser, UV, UVA, UVB, UVC, fluorescent and other very specific wavelength light. The cutting/slicing component fiber support stem provides photonic or electrical power for illumination at a selected light wavelength to the optical slide component sample for backlight or "condenser" light in a microscopy sense. The stem may be wrapped in fiber bundles so that separate or disparate wavelength light can be channeled in parallel or combination, thus allowing viewing and identifying harmful agents in low or no light confined spaces for different microbial matter. Some optical fiber can be used for a variety of other applications, including sensors and fiber lasers. In some embodiment many propagation paths or multi-mode fibers (MMF), or those that only support a single mode called single-mode fibers (SMF) are used for imaging for a variety of microbial matter.

Imaging and Microscopy

Analysis of bio-samples can depend the capability to focus on the depth at which the microbial or viral agents reside. Therefore selecting the optimal microscopy technology depends on a variety of factors.

Imaging depth is one of the most important microscopy optics considerations. Some biological processes occur at the surface, where cell membranes interact with their environments, while others happen deep beneath the surface. Specimen depth bio-matter at variable depth have must be accommodated. Light scatter, absorption, background signal, difficulty in collecting enough photons at the detector, and refractive index differences present a variety of challenges.

Various embodiments of the invention will have integrated components for a variety of optical path microscopes from Near Field Scanning (NFS), Stimulated Emission Depletion (STED), Photo Activated Localization Microscopy (PALM), Stochastic Optical Reconstruction Microscopy (STORM), Gated STED (gSTED), Fluorescence Correlation Microscopy (FCM), Time Tagged Time Resolved (TTTR), Confocal and other microscopy technologies for analysis insitu samples of biological or organic matter. Detector sensors and image production will be coupled with digital processing which can be local tool connected or wirelessly coupled to external processing and display devices.

An embodiment of the invention uses a window pocket to hold bio-matter, tissue, blood, body fluid, or sample for magnification and imaging. A window pocket is an enclosure having cutting edges with which sample can be collected into the enclosure or pocket from a biopsy or in situ bio-matter. The window pocket acts like a window to photonic illumination from one side of the collected sample, not unlike condenser illumination for a slide and into the optical magnification path of a microscope. Slides are typically manually made as well as microscopic observations, but the window pocket will automate the making of slides by application of a window pocket construction in concert with an optical magnification into an electronic image sensor.

FIG. 1 is a cross sectional view of an insitu bio-matter magnification device for digital analytics device in accordance to an embodiment of the present invention.

In a simple overview an embodiment having a device housing 101 contains, cutting edges on a window pocket for collecting bio assay into a two blade 101 121 window pocket component 122 supported by a fiber optic stem 118 having a far side window pocket 101 side with cutting edge perimeter, adjacent to and supporting a VCSEL array 103 for bio matter illumination from the side opposite the image detector. The VCSEL array 103 is powered by electrical or photonic conductor 107 for VCSEL array 103 illumination thru microlens array 105 providing photonic emission through a bio sample 119 and through a near side window 121 more or less parallel with the far side window 101 for containing the bio matter 119 within the illuminating pocket window and into an optical path for ultimate imaging. Illumination exposing the bio matter 119 will travel in the optical path to an CMOS image 117 processor and on to scanner image processing and stitching logic 110. Mechanism for component movement and power is provided by motor 115 with power transmission 113 coupled to the housing 102 is controlled by logic 110 internally mounted inside the housing 102.

In an embodiment of the invention, the window pocket is an optical two cutting edge slab component forming a sample collecting enclosure coupled to an optical or electrical channel coupled stem coupled to a housing, stem rotatable and extensable-retractable under digital logic control. The device is contained is a housing having an optical and digital magnification path coupled to image detecting sensor and logic, with a window pocket structurally coupled to a stem. The window pocket component has an open enclosure with cutting edges for collecting bio sample, with window pocket providing photonic illumination source from a side of the collected sample and into the optical and digital magnification path. The stem has at least one fiber optic channel for conducting selected pulsed or streamed frequency and wavelength light from single wavelength or tunable wavelength light sources into the window pocket.

Figure 2:
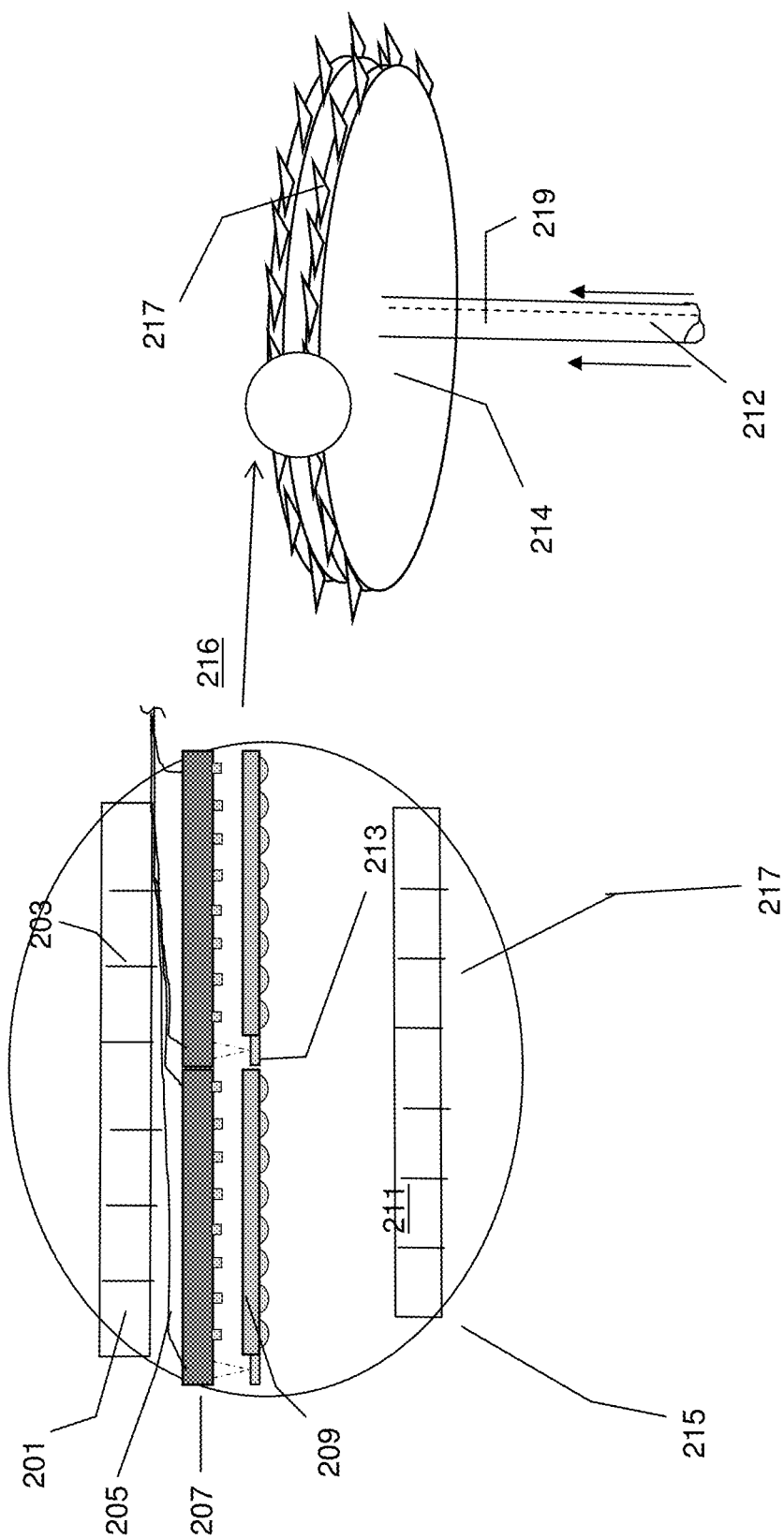
FIG. 2 depicts a two blade window pocket slide with cutting edge perimeters, according to the embodiment of the present invention.

FIG. 2 illustrates a two blade window pocket with cutting edge perimeters for bio matter optical magnification, according to the embodiment of the present invention.

A bio assay slide holding window pocket component 214 is rotatably coupled to a fiber optic stem 219 conducting photonics and or electrical power for illumination 212 through a cutting edge 217 window pocket 216. A window pocket having a flat far side slab 201 rigidly coupled to a VCSEL array 207, where the laser illumination power is arranged in parallel in the direction perpendicular to the substrate slab, with a far side slab having a cutting edge perimeter rotatable for cutting. A near side slab 215 also having a cutting edge 217 perimeter, with near side slab window pocket parallel to but offset from the far side window slab 201. In an embodiment of the invention a VCSEL array 207 can be powered by electrical connectors 205, electrical conduction layer or by photonic fiber 219. for the purpose of emitting back lighting through a parallel layer microlens array 209 and through a bio assay 211. In some embodiments focus alignment spots 213 may be interspaced with the microlens array 209. Adjustable frequency and intensity light emitted through the bioassay or sample layer 211 flows through the near side window slab 215 for focus, magnification and imaging downstream.

Figure 3:
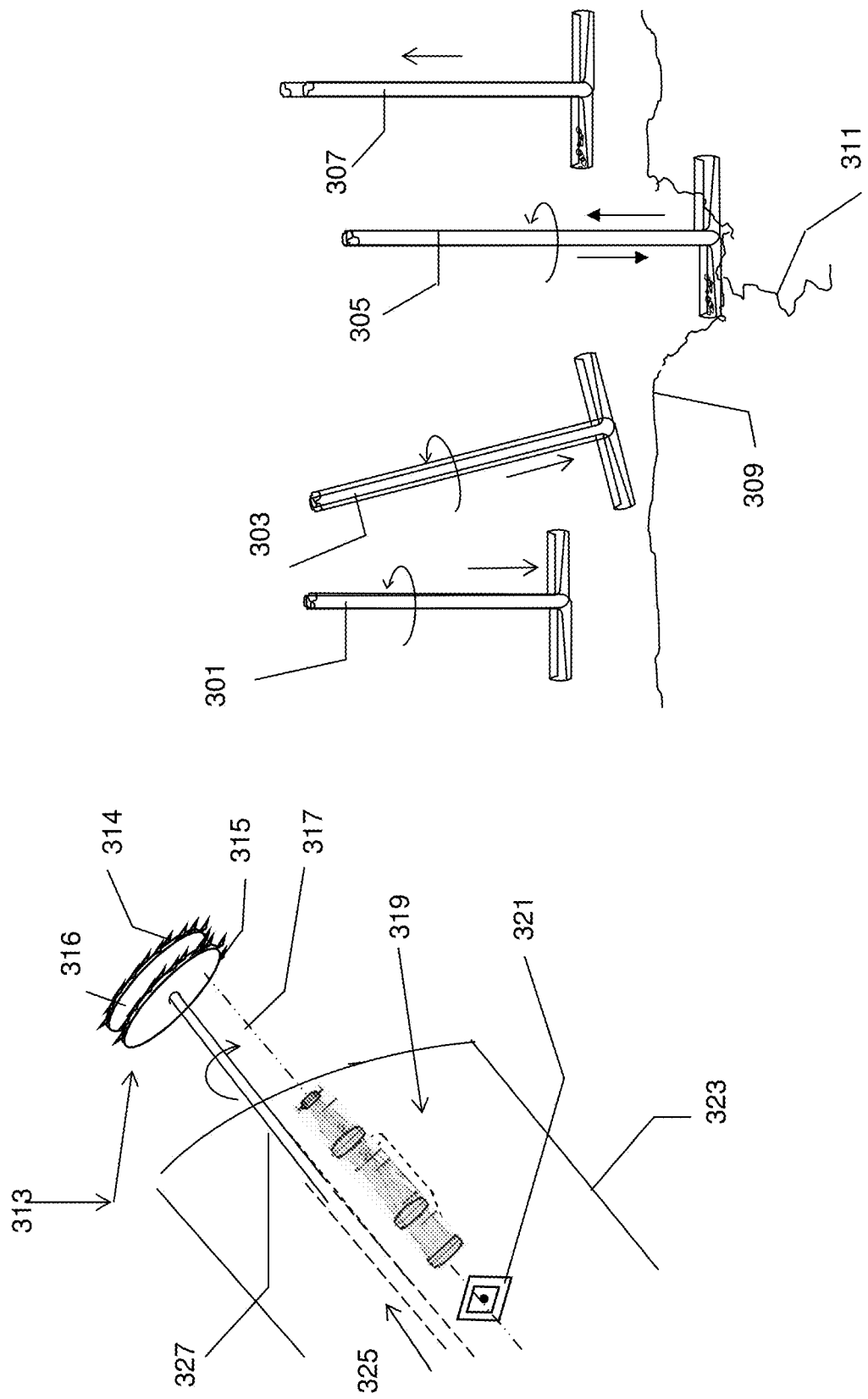
FIG. 3 is symbolic component illustration of a compound microscopy optical path through an vivo slide sample, according to the embodiment of the present invention.

The window pocket component is optically coupled an electro/optic channel stem distal end, for conducting selected frequency light from the housing to a window pocket side normal axis surface for illumination penetrating a specimen sample in the window pocket for optical imaging into an optical microscopy magnification path axis with an optical microscopy magnification path magnifying and focusing images on a digital CCD or CMOS detector, FIG. 3 is schematic illustration of a compound microscopy optical path through an vivo slide sample made with backlight illumination through a two blade window pocket, according to the embodiment of the present invention.

In an embodiment device housing 323 having source phonic and or electrical power 325 for sample bio assay illumination, light and or power is channeled via the stem 327 optical fiber or conductor into and through the two blade window pocket slide gap 316 where bio matter may be carved from biopsy cell scale and lodged in the optical two blade window pocket, far side 314. The two blade window pocket for creating a slide 313 for magnification and digital image has at least two sides, a side 1 or far side 314 is furthest away from the optical lens path 319 and a side 2 or near side 315 which is nearest the optical path 317 lens. Light is emitted from the normal two blade window pocket 313 surface through bio-matter 316, emerging light from a near side surface 315 and into the microscope 319 optical path. The optically magnified object is focused onto the CCD or CMOS detector 321 which magnifies the image into a micrograph image which may further magnify through electronic or pixel image expansion. The optical path 319 illustrates an optical compound microscope magnification. In other embodiments alternate microscopy optical paths can be used serially with digital zoom for even higher magnification. A two blade window pocket stem 327 is mechanically controlled to slice out bio tissue sample and then retract to a good focal point position in front of the optical path 319 front end lens.

In a simple embodiment housing 323 can be from various materials and construction. Silver, a germ resistant material and can also be used as a jacket in an embodiment of the invention housing to retard or prevent material infection transfer. Other methods and materials can be used for the housing to ease cleaning and insure adequate disinfection of the tool.

In an aspect of a two blade window pocket slide in vivo sample collection, a two blade window pocket 301 302 is inserted into the tissue 309 and pushed manually or mechanically into the sample 311 for collection. Some manual or mechanical rotation and displacement opening in/out motion from the window pocket stem motion will collect some tissue samples 315 onto the optical pocket 316. In an embodiment the two blade window pocket 321 will have two cutting leading edge window slabs 314 315 to better slice the biopsy tissue 315 into the optical light pocket 313 component. A mirror 314 on one slab with high reflectivity may provide a layer on the cutting slide microscopy far side of the optical window component 313 to reflect and channel light into and through the slide bio-matter 315 collected in the optical pocket and onto the microscopy optical path 317 normal to the optical window pocket 313 plane. In an embodiment laser/light is conducted through fiber 327 stem and into to optical window pocket 313, for light emission through the sample bio-matter 315. In an embodiment of the invention a rangefinder and control logic or proximity sensor guide the biopsy slicing window pocket to the target and upon sample recovery return the optical window pocket component to the housing focal plane for focus and imaging.

In another aspect of the invention Flexible OLED or AMOLED display on a silver grid housing may be used. A flexible display housing can be made from bendable plastic substrate, based on organic thin-film transistors (OTFTs), a main structure of the backplane made of polyethylene terephthalate (PET). In an embodiment of the invention a backplane can be laminated to a front plane, harnessing its electronic lighting display qualities technology with plastic logic transistors, display with embedded light frequency LEDs in flexible substrate. In another embodiment flexible circuits electronic components are mounted on, or printed on, flexible plastic substrates, which can be made of polyether ether keytone, PEEK, an organic thermoplastic, polyimide, or transparent conductive polyester film.

Joining optical fiber channel 327 to the two blade window pocket optical plate 313 portion must comply with the typical optical connectivity rules, whereby the ends of the optical fiber 327 must be carefully bent to retain contiguity, photonic transmission, and power, and then carefully spliced together with the core alignment to the window pocket bio matter 316 while fusion splicing using heat to fuse the ends of the fiber and plate slide two blade window pocket component together for reduced junction reflection and maximum transmission Other optical fiber connectors for temporary or semi-permanent connections can be used and may include semi-conductor substrate material with optical properties such as plate embedded edge emitting lasers or diodes.

The total magnification is the product of: the objective lens magnification, the optics magnification and the enlargement factor of the display media. For some embodiments a compound microscopy optical path for simple optical and digital detectors magnification range is acceptable for a typical Biopsy micrograph.

In an embodiment of the invention the objective lens is, a very high powered magnifying glass i.e. a lens with a very short focal length. This is brought very close to the specimen being examined so that the light from the specimen comes to a focus about 160 mm inside the microscope tube. This creates an enlarged image of the sample or bio-matter to be magnified for micrographic image purpose. This image is projected onto the CCD or CMOS camera in line 317 with the optical microscope. By carefully focusing a brightly lit specimen, a highly enlarged image is rendered onto the CCD or CMOS detector 321. It is this real image that is projected onto the detector that provides further enlargement, providing mechanism for digital zoom and focus on the virtual image. In other embodiments, images of different wavelength light can be detected using a multispectral line-scan camera. Multispectral filter optical components can be used for selected depths into a specimen sample, reconstructed post image processing. Optical coatings on the two blade window pocket slide component can facilitate the transmission of only certain wavelength light form certain image components.

In an embodiment of the invention surface emitting LED or semiconductor laser light from the slide surface is channeled through the optical plate two blade window pocket containing bio matter far side 317. In some embodiments of the invention the two blade window pocket optical slide far side 317 will have surface-emitting semiconductor lasers providing backlight. These can be in the form of vertical cavity surface-emitting laser, VCSEL, optically or electrically pumped output beams. For higher output power vertical external cavity surface-emitting lasers, VECSELs, can also be used along with other surface emitting laser/light technologies. In another embodiment of the invention vertical emission of light from the two blade window pocket slide surface can also be achieved with a edge emitting laser diode which is based on a waveguide along the chip surface as in an edge-emitting laser. Here light emission is in the vertical direction because the light is reflected upward with a 45° mirror, horizontal cavity surface-emitting laser, HCSEL. In another embodiment more than one laser/light channel 325 will emit conducted multi-wavelength light through the sample for various microscopy effects. In another embodiment photons of selected frequencies can be emitted from light sources 325 having logic with delayed image 321 scans for stimulated biomatter photon back scatter.

In a embodiment of the invention a high power VCSEL model can consist of several semi-conductor chips, with dimension of 1 to 10 mm, containing several tens to thousands of individual VCSEL in an array, coupled to a common heat sink forming a submodule with several packed together.

Figure 4:
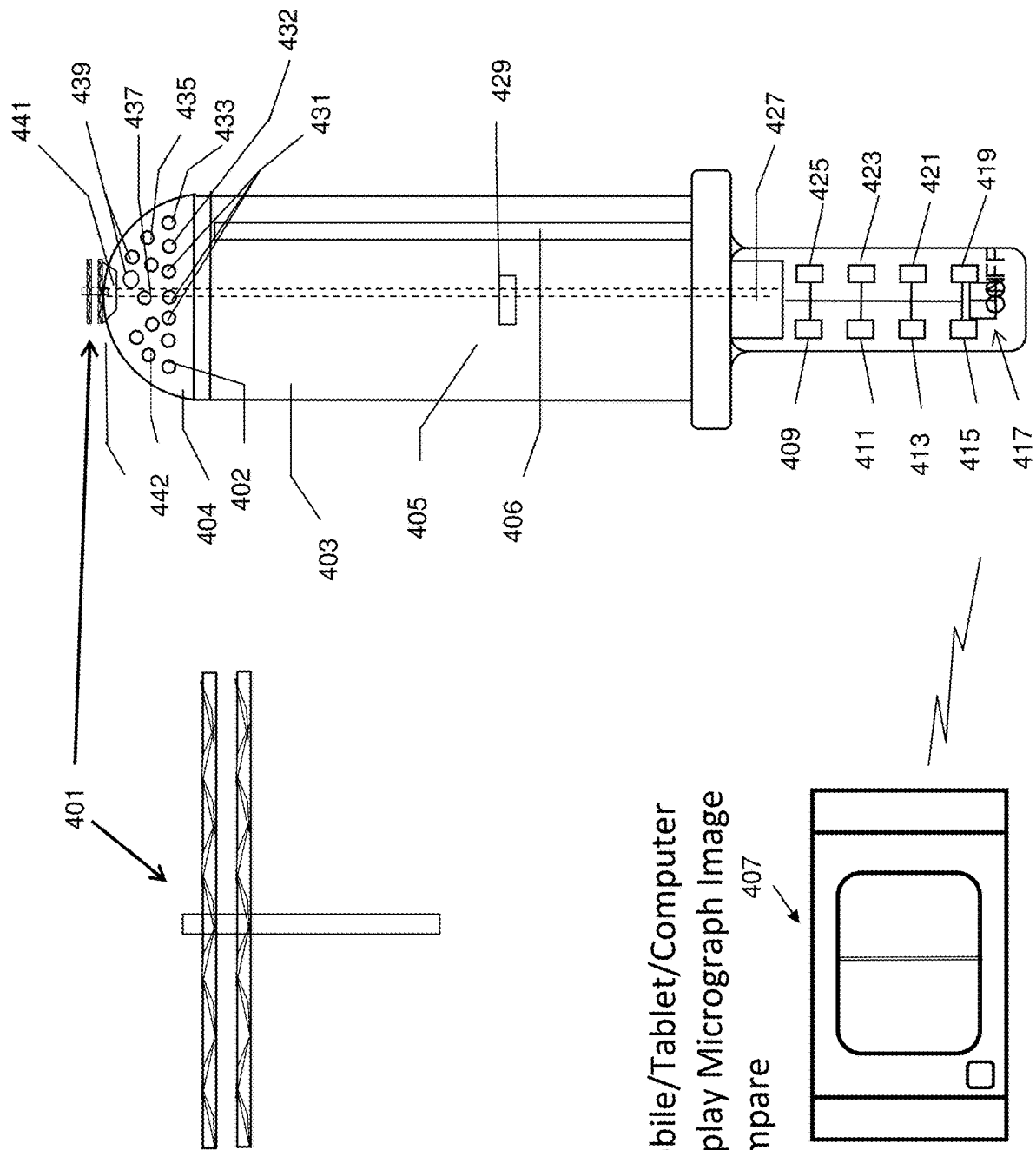
FIG. 4 is a component view of an biopsy micrograph creating device according to an embodiment of the invention.

FIG. 4 is a component view of an biopsy micrograph creating device according to an embodiment of the invention.

FIG. 4 is a component view of an in vivo diagnostic tool according to an embodiment of the invention. A housing 403 contains the components of the tool, extended from a handle 417 and ending in a top 404 outer portion from which an optical two blade window pocket optical pocket 401 coupled to an optical property stem 405 which can be extended outward from the housing 403 in various forms to enhance the biopsy bio sample collection. In an embodiment the stem 405 optical property can be a mono or multi-wavelength multimode fiber channel. In an embodiment an object optical lens 441 leading a set of lenses providing a microscopic optical magnification is aligned along an optical path normal to the two blade window pocket slide 401 surface. In another embodiment scattered light detectors 439 or 3D detector lens are positioned on the head 404. In yet other embodiments laser 435, proximity sensor or rangefinder 432, excitation laser 437, fluorescence laser 433 and or variable frequency LED array light sources are positioned on the tool head 404.

An optical path through the optical lens set is focused onto an image detector CCD 429. The image detector CCD or CMOS is electronically coupled to components and logic to process the image micrographs including program logic 409, memory 425, image processor 411, image storage 423, image comparator 421, CPU 413, wireless chip set 415 and power 417. The wireless chip set 415 and logic 415 409 facilitate wireless I/O to-from a mobile, tablet or computer 407 for display and more. In another embodiment, a CCD or CMOS imaging array 406 detector extends along the longitudinal housing to provide a cavity length dimension image or video sample. An intense CMOS multiplier or photonic counting CCD may be used in embodiments where illumination is expected to be extremely low. A small window touch screen display 427 will provide control selections for verification, confirmation and basic user interface commands.

Local and wireless remote components for display of two blade window pocket micrographs and identified matching images, are coupled to display from mobile, tablet, phablet, computer screen, and local tool small window and 3D displays.

In an embodiments of the housing 403 the dimensions will be such that the tool will be inserted in vivo depending on the tissue to be reached. In some embodiments the housing outer material will be physically compatible with human tissue and human cells, capable of adequate cleaning, disinfection and sterilization processing.

Various sources of light can be used in microscopy embodiments depending on requirements for the microscopy optical paths applied. In a simple embodiment, visible lamp light, multi-wavelength, LEDs or laser light will illuminate the target sample by conducted mono or multi-mode fiber optic light to an optically conductive biopsy tissue two blade window pocket component having surface emitting optical character. The two blade window pocket component light is conducted from the two blade window pocket stem and through the two blade window pocket far surface. This two blade window pocket portion has optical properties for the photonic functions but can also be of semi-conductor material for enhancing emission of laser light through its normal surface, providing a light source serving as the condenser backlight traveling through a specimen on the two blade window pocket surface.

In another embodiment of the invention, far side of the optical two blade window pocket slide has a reflecting mirror on the two blade window pocket component far side reflecting any internal light back towards the near side surface containing the sample. This optical two blade window pocket component surface 401 emits backlight through the microscope specimen acting as a condenser lens designed to focus light from the illumination source onto the specimen scraped from the tissue wall onto the optical two blade window pocket surface or pocket. The optical two blade window pocket condenser lens may also include other feature as such as a diaphragm and/or filters, to manage the quality and intensity of the light in the cavity visited, here the vagina towards the end adjacent and centered on to the cervix opening. For special illumination techniques, additional optical components must be precisely aligned in the light path from the specimen to the objective lens 441, pin hole 442 or photon counting/imaging detector 402. Some invasive cancers can penetrate the tissue making them undetectable to visible inspection. Fluorescent biomarkers can help reveal these. Photon counting and imaging provides an alternate capability where the scattered or reflected extremely low-light conditions require some tissue penetration. ICCD or EMCCD image detectors would convert the photons to electrons and then back to photons for counting purposes in the total internal reflection fluorescence, TIRF, optical path. These light sources can be positioned on the housing distal end having internal cavity projected light sources from laser, IR, UV and LED for accommodating disparate scattered light microscopy optical paths.

In an embodiment of the invention the actual power or magnification of a compound optical microscope is the product of the powers of the ocular and the objective lens. The maximum normal magnifications of the ocular and objective are 10× and 100× respectively, giving a final magnification of 1,000× not including the digital power magnification.

An inline CCD or CMOS camera with pixel size and number of the pixels in the detector provide yet another enlargement factor. A typical Biopsy stained cervical cell image, acquired through a CCD camera adapted to an optical microscope will require at least a 40× magnification lens and images stored in digital media format having size 2048× 1536 pixels. Digital magnification can be 5×-20× and the enlargement factor approx 5×. So the optical magnification of 40× means that smaller optical path and girth dimensions are within the housing or human cavity range.

Figure 5:
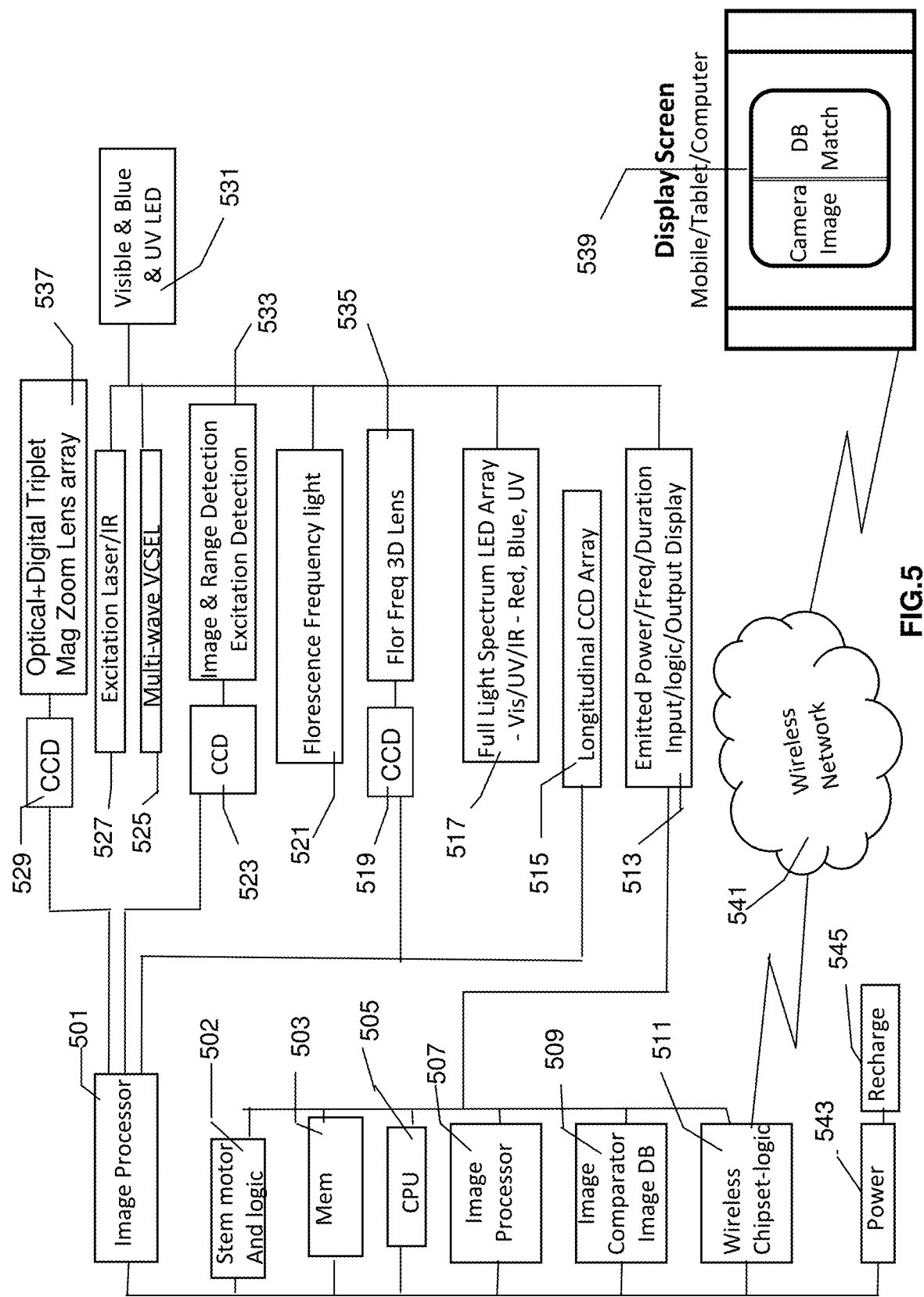
FIG. 5 is component block diagram of a biopsy micrograph creating device according to an embodiment of the invention.

FIG. 5 is component block diagram of a biopsy micrograph creating device according to an embodiment of the invention. There are at least two different aspects to the laser/light sources. The first is for illumination of in vivo obtained slide samples or targets from the cervix through back lighting, substitution of the lab microscope condenser with the two blade window pocket optical component. The second major feature is the illumination or exposure of the tissue from above without use of the two blade window pocket tool but with microscopy optical path methods using scattered light.

An embodiment of the invention can contain some or all of the electronic components including CCD image input processing 501, motor control logic 502 of the stem for sample collection\ and focal plane positioning, basic computer memory 503, a control program executing CPU 505, image formatting processor 507, image real-time depth composition and high frame rate scans through a focal range of a sample to recognize areas of focus to build a fully-focused image programmatically, image comparator with stored image library or downloadable image micrographs which in some embodiments can include laser/light frequency/duration/power requirements for therapy application. Couple with the electronic components of an embodiment are wireless chip set 511 using any available wireless protocol to a wireless network 541. Power 543 source and/or recharging 545 capabilities provide electrical power to the tool.

In an embodiment of the invention applying laser/light sourcing from a tunable laser may be used. CO2 laser has been used to treat cervical squamous intraepithelial lesions (SILs). In an embodiment of the invention, after confirmation with a cervical biopsy image micrograph, appropriate therapy light treatment for a beam of infrared light with the principal wavelength bands centering around 9.4 and 10.6 micrometers can be applied. The tunable frequency laser having CW powers in milliwatts, mW, can be used. A laser producing a beam of UV or infrared light with the principal wavelength bands centering around 9.4 and 10.6 micrometers are integrated in some embodiments to identify some SILs.

In laser or light source aspect embodiments, to determine the laser power density output requirements, one method is to calculate the area over which the laser/light will distribute power, milliwatts, and programmatically insure that the illumination delivered to the target area is below allowable and set power applications. In some embodiments this will be automated in logic and in other embodiments physicians will be provided flexibility in applying alternate microscopy methods to an individual and specific patient. If the laser is calibrated to a known intensity, milliWatts, mW, in continuous mode, the target size can easily be adjusted to provide the proper power density by positioning the laser light source. A camera image without magnification can be used to ascertain the exact area for application and the power therapy requirements can be from known data and local geometry, for optimal illumination over a specific area. The three factors to be considered in the laser/light source are the 1) laser power, 2) length of time for which the laser intensity acts, and 3) area size on the tissue. Knowing the laser power and the area subtended, the time can be calculated and set by default for an automatic programmed pulse working in concert with image intermittent takes. CCD imaging logic can be used with Time Tagged Time Resolved (TTTR) methods to obtain yet finer images for smaller entities.

Different bio-entities of different size, scope and range dictate that several laser/light sources and modes be available for the tool optical path. In some embodiments one or more laser/light sources including an Excitation Laser/Infra Red 527, Multi-wave VCSEL 525, Fluorescence frequency light 521, full light spectrum LED array 517 for visible-Red, Blue/UV/IR frequency light are available sources.

Detectors and sensors include and optical/digital triplet magnification zoom lens array with CCD or CMOS 529, Image, range detection and excitation detection with CCD 523, Fluorescence frequency 3D lens set and CCD 519, longitudinal CCD array 515 detector for a cavity length wise scan. The housing may have a power/frequency/duration output display from control logic 513 for the emitting laser/light 527, 525, 521, 517 light sources. The wireless 511 connectivity will have display screen 439 variability to mobile/tablet or computer screens.

The image detector electronically coupled to electronic imaging logic for processing and display of micrograph images, with logic for digital control, image focus and image processing of images responsive to the stem and optical path positioning. There is also display of image processing results locally or wireless transfer to remote digital display device, whereby image comparisons and analytics can be accomplished and resulting digital image micrographs from optical two blade window pocket collection programmatically processed, identified and verified in situ in real-time.

The optical microscopy magnification path is selected from a group of microscopy optical paths including single lens, compound lens, confocal, TIRFM, Photonic, and Fluorescent. A coupled optical window transparent to selectable wavelength light from a group of light sources can be from visible, red, blue, UV-A, UV-B, UV-C, LED, excitation laser, fluorescent, full spectrum, multi-wave and Infra Red. Illumination from window pocket slide can be from normal to the surface emitting light from a set of surface emitting light components consisting essentially of VCSEL, VXSEL, edge emitting laser diode, surface laser, internal mirror.

Figure 6:
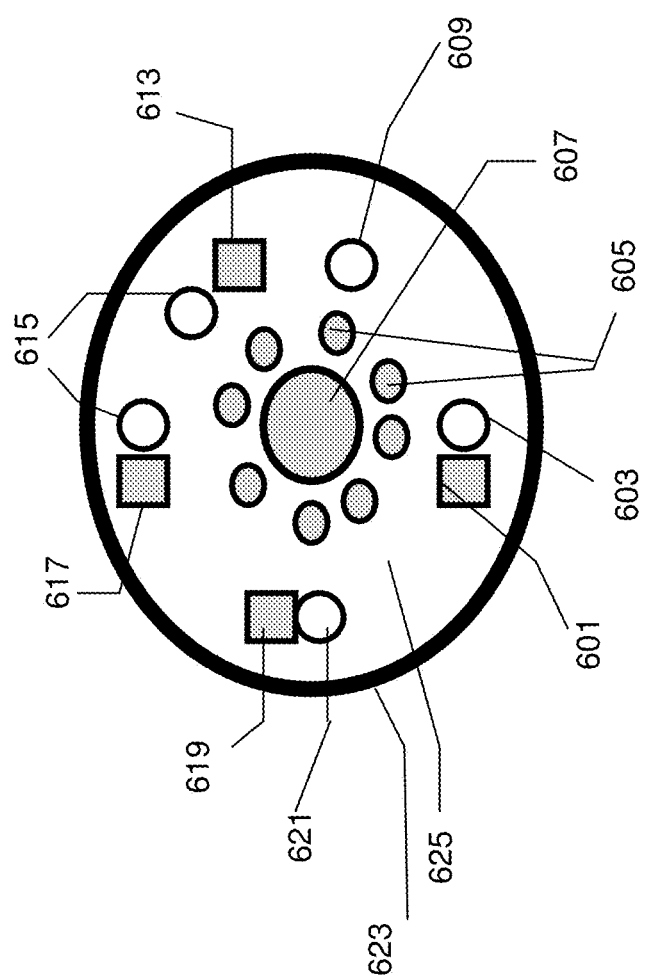
FIG. 6 is an front view illustration of a biopsy micrograph creating device according to an embodiment of the invention.

FIG. 6 is an front view illustration of a biopsy micrograph creating device according to an embodiment of the invention. In an embodiment of the invention a device housing 623 has an internal cavity facing end 625 which contains an integration of detectors and laser/light sources. An optical lens 607 resides in the optical path center and is surrounded by an array of various frequency LEDs 605. An optical two blade window pocket slide opening 607 for an extendable optical two blade window pocket aspect of the invention which provides an in vivo specimen on a "slide" for microscopic scrutiny and image magnification. Other optical return paths 609 may be offset for other microscopy methods such as NFS, STED, PALM, STORM, gSTED, FCM, TTTR, Confocal and other microscopy technologies. For this and other reasons a range of frequency LEDs outwardly facing may include UV-C 603, UV 621 and or with laser 617 613 601, IR 615 at various locations for reaching determined areas subtended.

Figure 7:
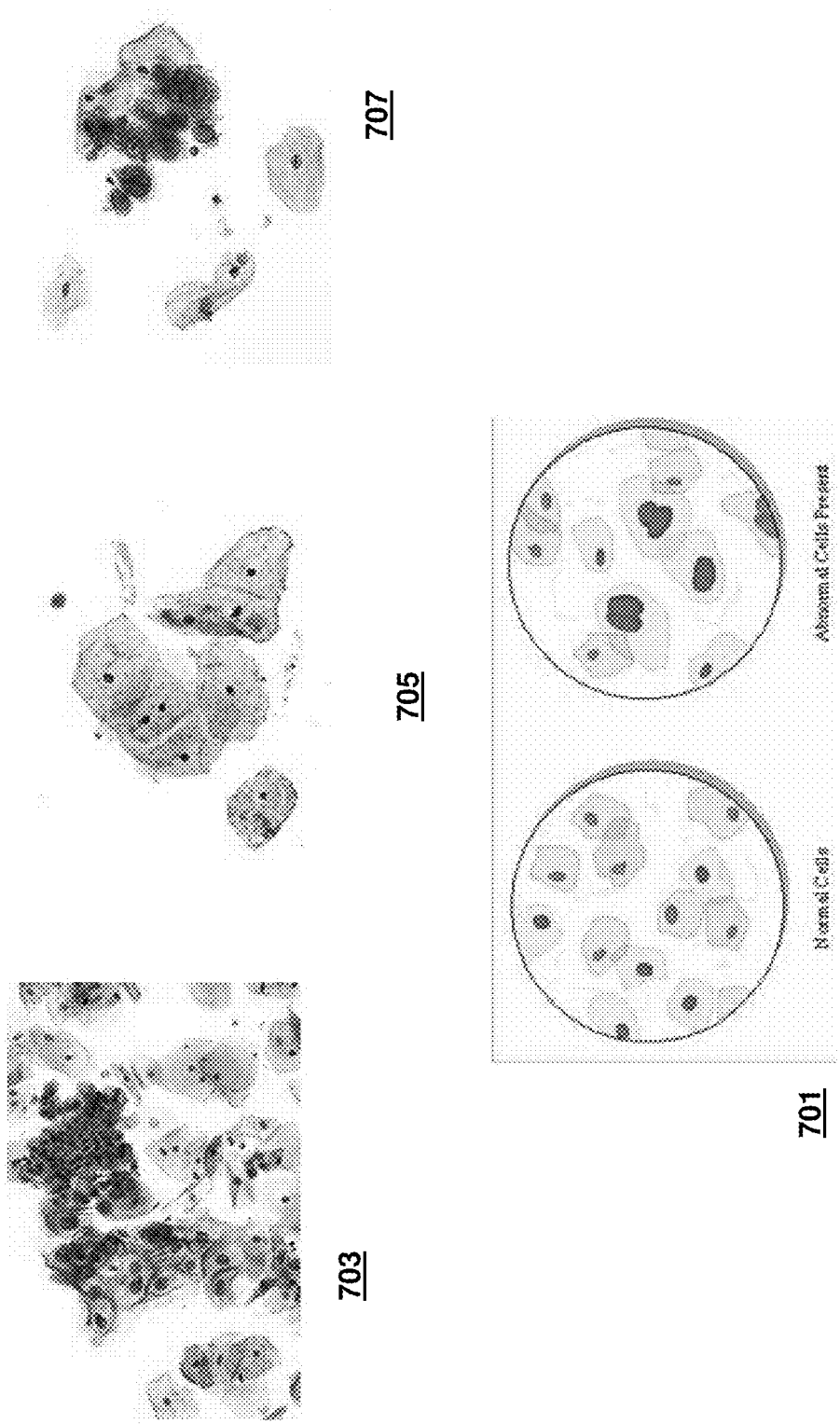
FIG. 7 illustrates in vivo images for bio specimen comparison analysis of abnormalities from biopsy micrograph creating device according to an embodiment of the invention.

FIG. 7 illustrates a biopsy image for comparison analysis and identification of collected sample abnormalities for in vivo device images for pathology exam according to an embodiment of the invention.

Pathological or AI image analytics may begin with obtaining a digital micrograph of a specimen for comparison with stored known images of lesions, and other abnormalities or harmful bio agents. Optical two blade window pocket or probe obtained micrographic images are processed by image analysis and compared against known images for identification and potential hazards. In an embodiment of the invention FIG. 7 images are digitally compared against local or remote image stored and compared for biopsy micrographs showing low-grade intraepithelial lesion (LSIL) 703 and benign endecervical mucosa, Trichomonas organism 705, herpes simplex virus 707, and any of the known pre-cancerous or cancerous agents in the form of normal to abnormal cell 701 micrographs. Carcinoma, Melanoma, Basal Cell and other cancers and cancer precursors can be identified by such processes.

The step of identification of harmful agents provides obtaining an image of the offending microbial specimens including Endocervical adenocarcinoma, Candide organisms, viral cytopathic effect consistent with herpes simplex virus, normal squamous epithelial cells in premenopausal women, atrophic squamous cells in postmenopausal women, the cytoplasms of squamous epithelial cells melted out, Infestation by Trichomonas vaginalis, obviously atypical cell, HPV legions and other anomalous or symptomatic characteristics, legions, anomalous growth. Identification of the offenders requires creation of micrograph images of different bio-matter sizes, different magnification, and sometimes in different depth in the tissue. Detection therefore accounts for all of these but in some embodiments the scale and scope of the tool will determine which biological entity is sought.

In addition to the typical biopsy bio-matter of diagnostic import are sexually transmitted diseases. These including *Chlamydia trachomatis, Neisseria gonorrhoeae, Treponema pallidum, Ureaplasma urealyticum, Haemophilus ducreyi* and other such bio-entities are prime imaging diagnostic candidates. Urinary tract infections including *Escherichia coli*, other Enterobacteriaceae, *Staphylococcus saprophyticus, Pseudomonas aeruginosa* are more bio-entities which are potential image diagnostic bio entities for identification for remedial treatment.

Laser-based imaging is relatively incorporated into an aspect of the invention. Laser based imaging embodiment provides a combination of non-toxic gold nano particles and light to viscous specimens containing mucus or mucus like substances to obtain better images. In an embodiment of the invention specimen viscosity-thinning agents can be placed in or on the optical two blade window pocket component surface for improving specimen flow and specimen image collection.

Figure 8:
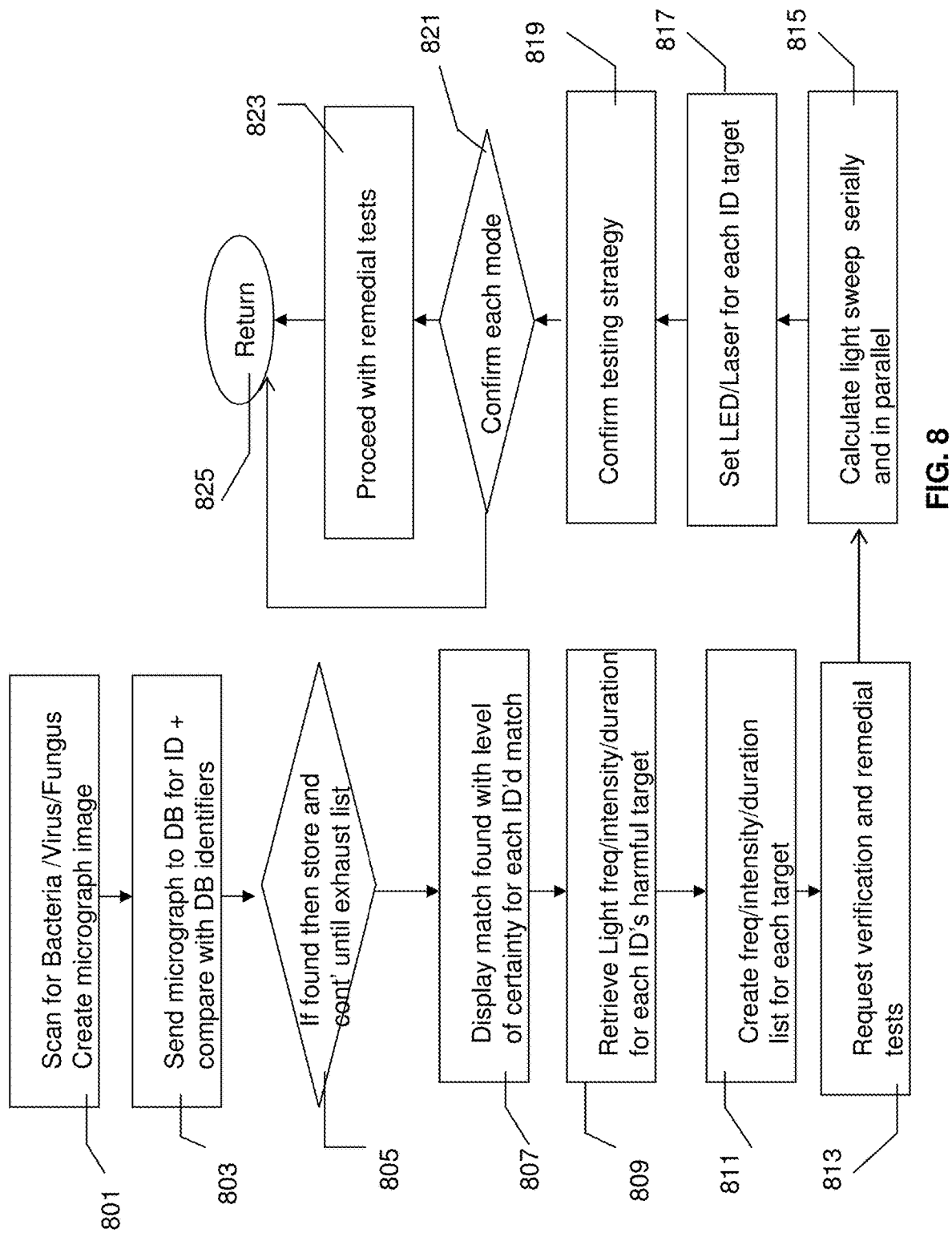
FIG. 8 is a process block diagram processing for biopsy micrograph creating device according to an embodiment of the invention.

FIG. 8 is a process block diagram processing for biopsy micrograph creating device according to an embodiment of the invention.

Diagnosis for harmful agent targets includes a series of steps for ascertaining harm for remedial subsequent action. A two blade window pocket specimen or probe image scan 801 is made to create the micrograph image for detection and identification. The optical image is then transferred to digital 803 to obtain specimen micrograph which can be compared against locally stored or remotely stored images. For efficiency, a plurality 805 of micrographs can be made to identify one or more harmful agent targets. Many digital image processing algorithms exist and are currently employed in identifying harmful agents, some more common are shown in FIG. 7. The micrograph image can be displayed and or stored when matches are found 807. In subsequent remedial modes, sequence for each identified match are retrieved from the a database or library 809. Order and the number of runs 811, serial or parallel threat removal, is programmed in to cover all match threats in a programmed sequenced light scans 815 after confirmation 813 and verification, where possible and in series where resources collide. In an embodiment of the invention an endoscope can be integrated into a optical stem to facilitate some procedures of obtaining an image and identifying the targets. A final confirmation 819 may be required by the physician.

An abbreviated step sequence implements a variable light frequency programmable for targets method using computer pattern matching images with known micro entities includes the steps of: 1) Scan and Identify the harmful target images, 2) obtain image and send for ID match in library database (DB), 3) compare with DB specimens, 4) Display found matching image on screen, 5) request type of light frequency required upon confirm at programmed power/freq/duration.

Essentially, logic for programmatically selecting and controlling intensity, frequency and power light sources which can be directed into insitu bio matter targets identified for the micrograph image processing is used to better highlight the sample characteristics and attributes for better identification.

Figure 9:
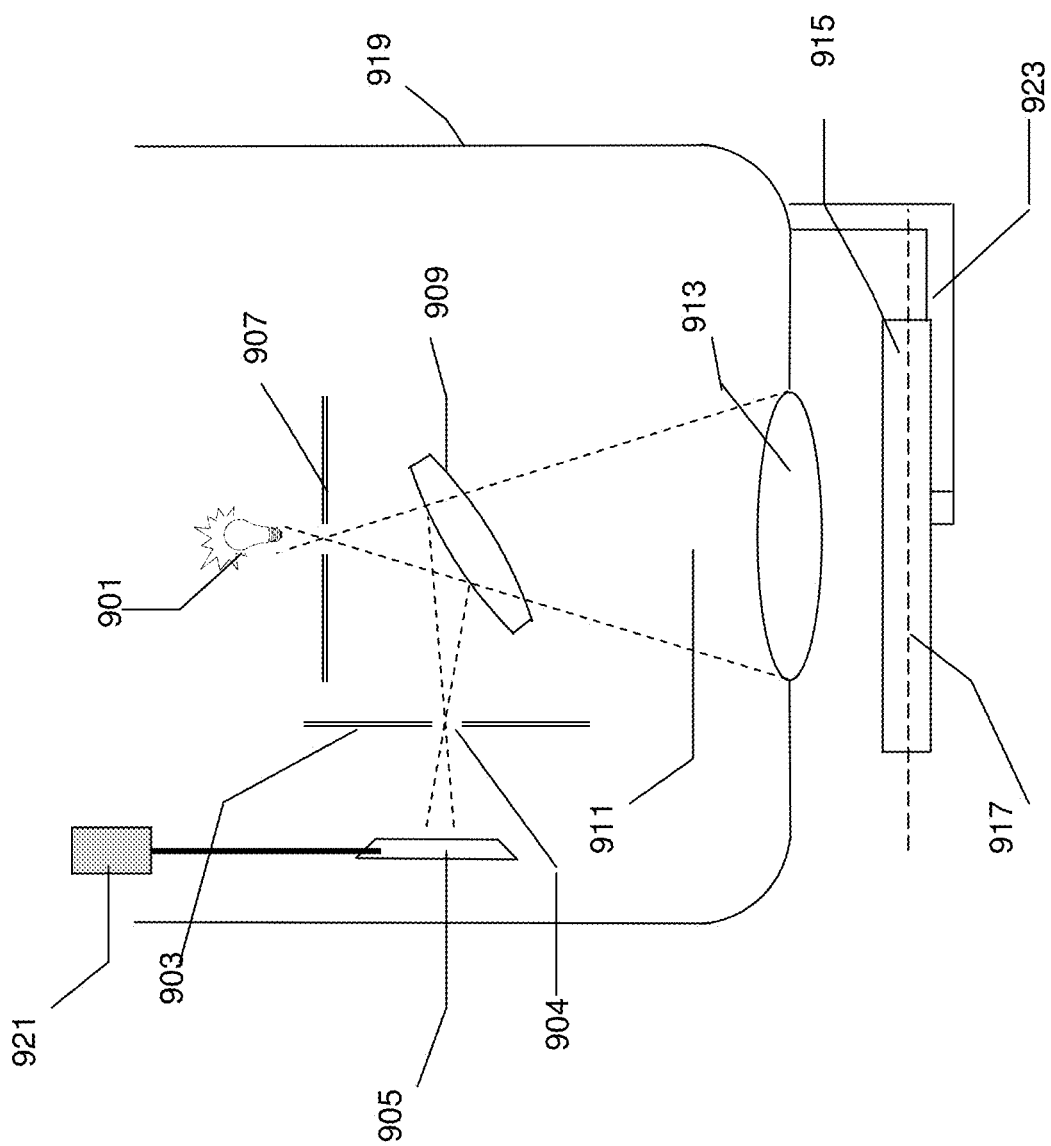
FIG. 9 is component level illustration of a con-focal optical path biopsy micrograph creating device according to an embodiment of the invention.

FIG. 9 is component level illustration of a confocal optical path biopsy micrograph creating device according to an embodiment of the invention.

Confocal microscopy imaging embodiment is yet another optical imaging path for increasing optical resolution and contrast of an in vivo micrograph by means of adding a spatial pinhole 904 placed at the confocal plane 903 of the lens 909 to eliminate out-of-focus light.

A confocal microscope configuration embodiment uses point illumination and a pinhole 904 aperture in an optically conjugate plane 909 in front of the detector to eliminate out-of-focus signal. The optical path 911 is channeled through a beam splitter 909 and into the detector 905 via aperture 904. As only light produced by fluorescence very close to the focal plane 917 can be detected, the image's optical resolution, particularly in the sample 915 depth direction, is much better than that of wide-field microscopes. The stem 923 is position controllable from logic coupled to mechanical motion controls and range finder or image input for focal plane focusing.

In an embodiment, points in the sample 915 on the optical two blade window pocket slide are illuminated sequentially. 2D or 3D imaging requires scanning over a regular raster CMOS or CCD 905, a rectangular pattern of parallel scanning lines, in the specimen 915, is then transmitted to the CCD 905 image processor 921. The achievable thickness of the focal plane 917 is defined mostly by the wavelength of the used light 901 divided by the numerical aperture 903 of the optical lens 913, but also by the optical properties of the specimen 915 on slide supported on the two blade window pocket stem 923. The light source 901 can be LED or tunable laser to provide the optimal wavelength required. In another embodiment the sample specimen 915 can be in vivo tissue and focal plane 917 can be the tissue surface or a depth within the in vivo tissue.

In another embodiment of the invention, lattice light sheet microscopy and light sheet microscopy configurations can be used. As shown, the illumination of the bio sample 915 occurs perpendicular to the imaging 911. Initially the light sheet is formed by stretching the linearly polarized circular input beam 923 with a pair of cylindrical lenses 913 909 along the perpendicular axis and then compressing it with an additional pair of lenses along the optical path axis (not shown). The image is then projected onto a binary ferroelectric spatial light modulator 905. The spatial light modulator 905 spatially varies the waveform of a beam of light. The light that is reflected back from the spatial light modulator 923 is used to eliminate unwanted diffraction as the light sheet is oscillated within the perpendicular axis 917.

In a dithered mode, the light sheet is rapidly scanned along the perpendicular axis and only one image is recorded in the optical or normal plane. In a second mode of operation, structured illumination microscopy mode, a grid pattern of excitation light is superimposed on the sample 915 and rotated in steps between the capture of each image. Thus the photon frequency and florescence source modulation and control for sample scanning is effectuated by the logic residing in the housing.

Figure 10:
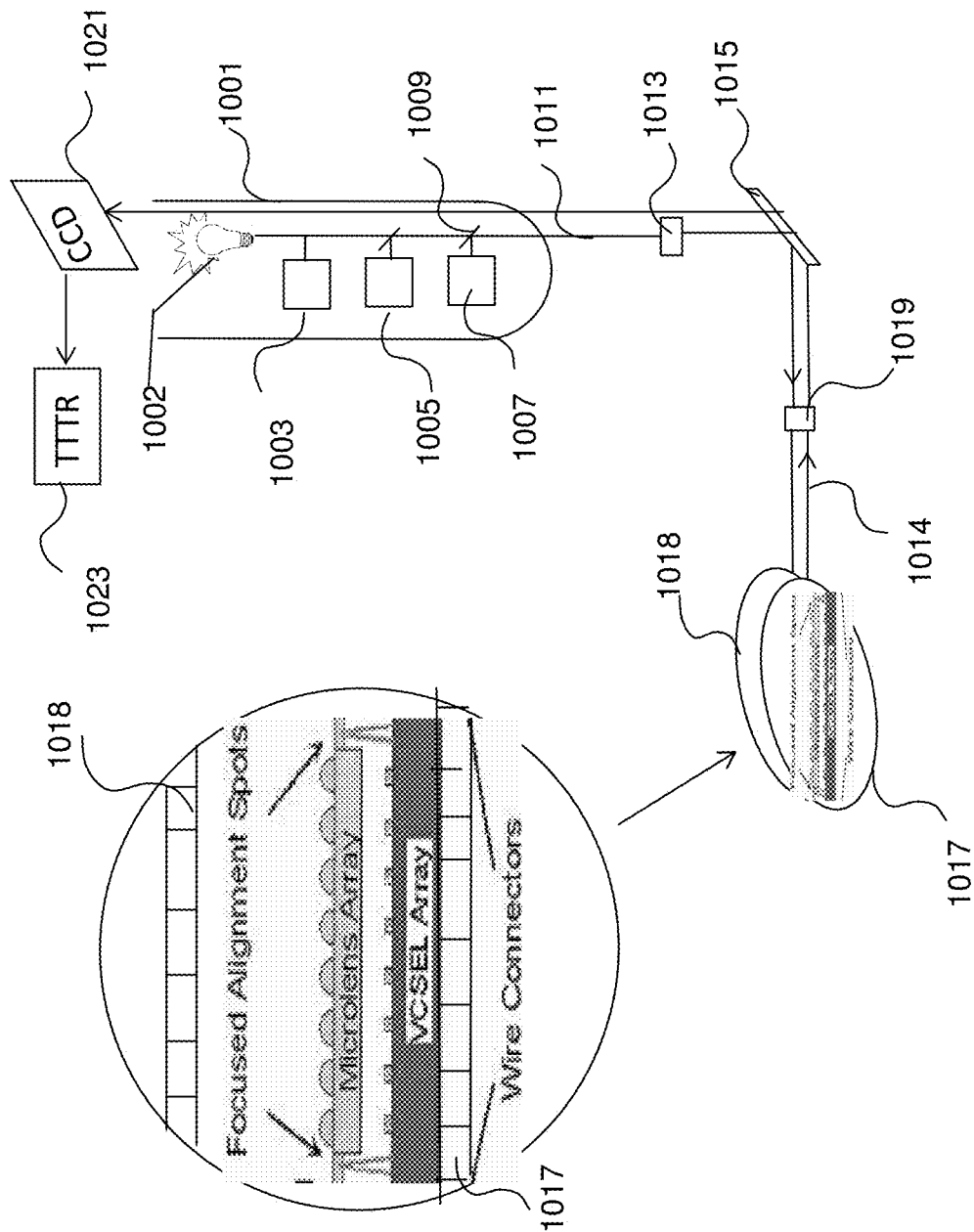
FIG. 10 is symbolic component level illustration of a TIRF optical path of a biopsy micrograph creating device according to an embodiment of the invention.

FIG. 10 is symbolic component level illustration of a TIRF optical path of a biopsy micrograph image creating device according to an embodiment of the invention.

In another embodiment, smaller organic entities or biomolecules requiring identification and examination of proteins in vivo will dictate higher power magnification or even lower illumination conditions. In some embodiments digital imaging detection such as Intensive CCD or Electron Multiplying CCD, may thus substitute for some optical path embodiment components providing images to the detector CCD 1021, ICCD, sCMOS or EMCCD, where prescribed for extremely low-light higher powers and resolutions using the optical configuration for Total Internal Reflection Fluorescence, TIRF. These in turn call for high-intensity laser to trigger molecular fluorescence. In another embodiment where added sensitivity of the camera is required, EMCCD 1021 photo counting imaging microscopy complete with optical path embodiments can be implemented. In yet another embodiment a Total Internal Reflection Fluorescent Microscope, TIRFM, is used sourcing an evanescent wave 1002 to illuminate and excite fluorophores on the slide surface 1018 when the incident light is totally internally reflected from the two blade window pocket slide surface 1018, penetrating to a select sample depth and returning signal in a parallel return path 1014 eventually to the detector 1021.

In some embodiments the optical path may require further optical and electronic components in the optical channel beginning with a light source 1002, excitation laser 1005, STED 1007, and single or multi-mode fiber channel 1011, a quarter-wave plate, dichroic mirror(s) 1009 1015 for frequency selection and filtering, segmented phase plate 1019, sample slide glass 1017 and return signal path 1014 to a detector 1021 and timed processing, TTTR, 1002. Logic and motor control 1003 of the optical two blade window pocket plate is needed for obtaining desired in biopsy sample specimens.

Figure 11:
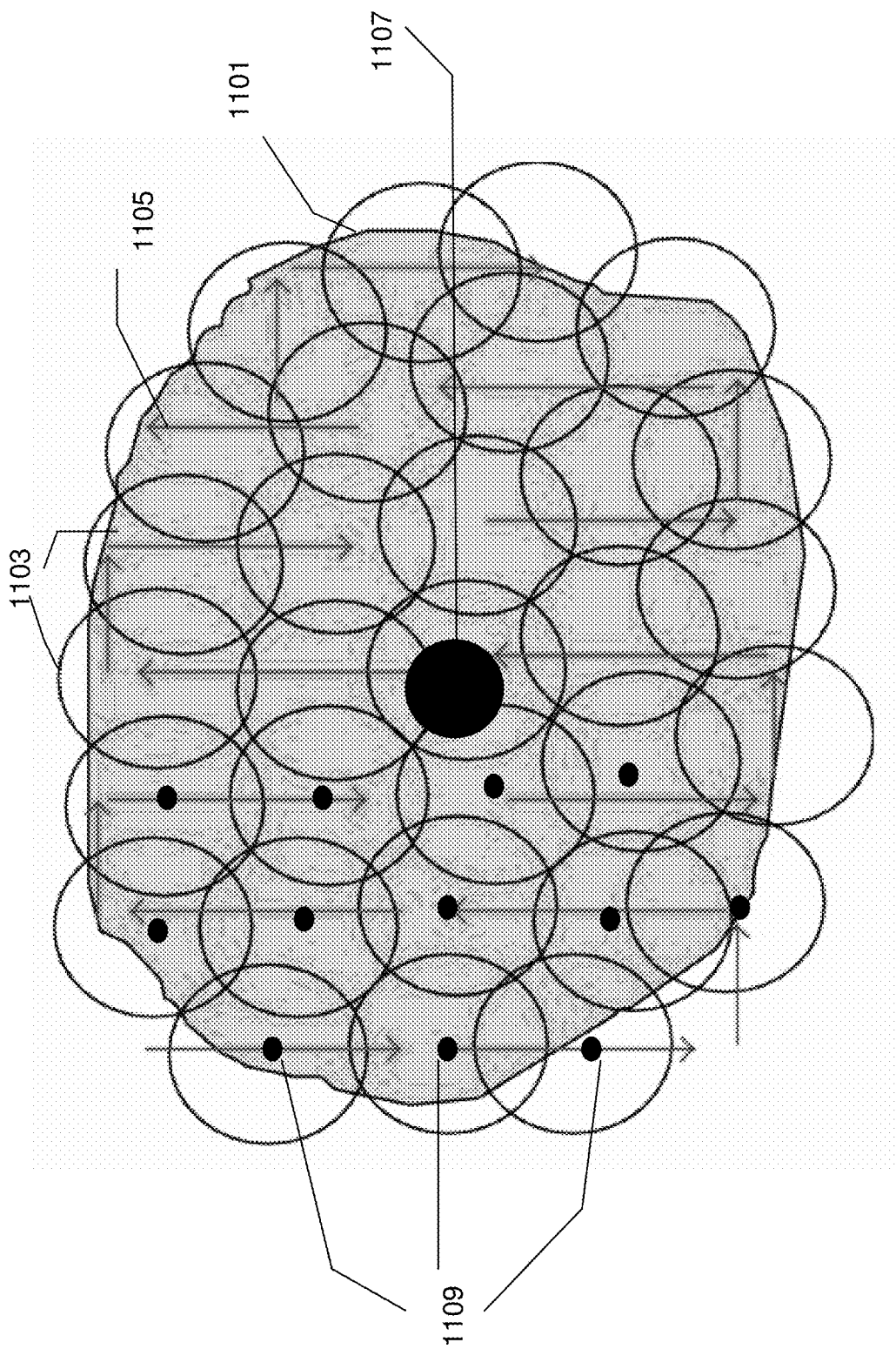
FIG. 11 is a schematic for micrograph image zones stitched together in a pattern to include an entire taken biopsy from a biopsy micrograph creating device according to an embodiment of the invention.

FIG. 11 is a schematic for micrograph image zones stitched together in a pattern to include an entire taken biopsy from a biopsy micrograph creating device according to an embodiment of the invention. The stem center 1107 forms an origin for a pixel unit coordinate system having circular zones 1103 with some overlap. The zones 1103 each have centers 1109 which have known offsets from the origin 1107 and a given radius which define each of the zone boundaries in terms of pixel location from the zone center offset and likewise from the origin. The edge 1101 of the sample is also known from window dimensions translated to pixel units. The camera image zones are stitched together in a known pattern shown by the arrows 1105, knowing the image sequence and the coordinates of the individual zones, zone offsets and origin coordinates.

Figure 12:
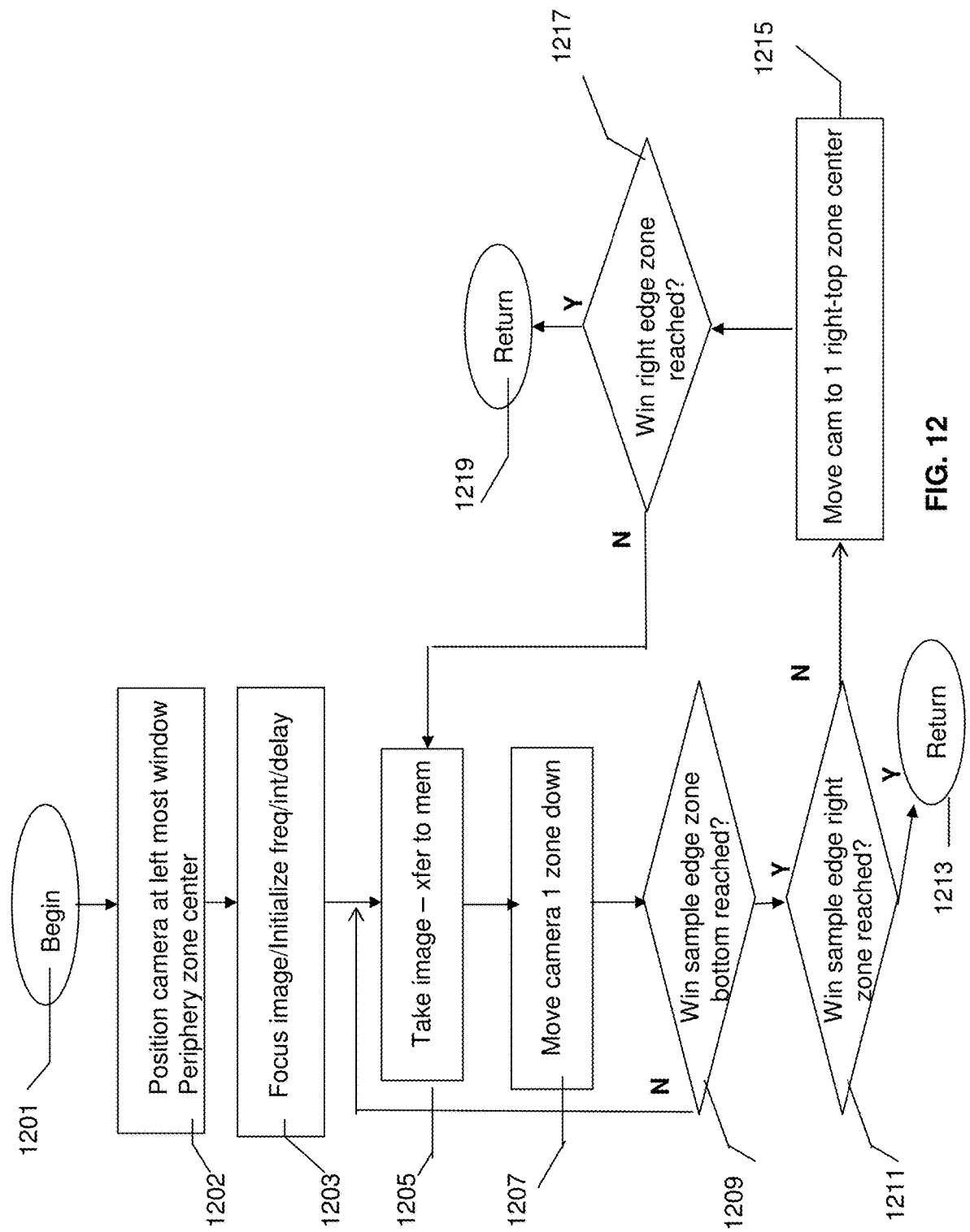
FIG. 12 is a flow diagram for defined micrograph zones stitched together in a pattern to include an entire taken biopsy from a biopsy micrograph creating device according to an embodiment of the invention.

FIG. 12 is a flow diagram for logic execution for obtaining a systematic sequence of images from defining micrograph zones stitched together in a pattern to include an entire taken biopsy from a biopsy micrograph creating device according to an embodiment of the invention.

An aspect of the invention will provide whole slide imaging slides to be scanned and viewed on a larger whole virtual microscopy image. The individual magnified images are digitally combined in a step ladder fashion to make sure that no window zones is missed. Multiple "circles" or zone images are magnified and combined from multiple overlapping areas of the window pocket bio matter sample. In logic commanding the stem manipulation responsive to image detection, a systematic pattern is made during the image capturing process. Each zone represents image snap shot. Multiple overlapping zones covering the entire tissue section in the window pocket are captured. Once the images are optimized and saved, they have to be merged to obtain a seamless collage of microphotographs which are perfectly aligned and merged to create a high resolution digital image of the entire section.

A window pocket geometry is laid out and mapped to a grid from the stem center at the origin, with image pixel units to the right and left of the origin with overlapping zones of mapped image snap shot or micrograph pixel unit zone radius, zones uniformly covering the entire window pocket with zone centers along more or less uniform offset x horizontal and y vertical lines. Logic with stem fine manipulation server motor control responsive to window focus zone centers, is executed upon user command to uniformly micrograph and stitch the micrographs together into a digital slide for transport, display and analytics.

An aspect of the invention having logic begins 1201 by motor commands to position the window for camera optical path centerline at left most window periphery zone 1202, or to position optical lens at the window pocket left most edge zone center offset from the stem origin coordinates.

Logic executes stem motor commands responsive to image focus markers and snap shot zone sequence will focus optical lens path to image sensor 1203 on the zone centerline marker in a systematic pattern to cover the entire window pocket area. Upon position and focus completion, photon sources will Initialize lighting frequency and intensity and delay time, delay time for image scan from time of photonic emission.

Having camera ready and in position with programmed zone centerline, a camera image is taken 12105 and the image copied to stitching memory which will have multiple image scan pictures to a larger window pixel size grid pixel unit map. Following a snap shot, motor commands will move the stem to position the window pocket zone increment one centerline below or on the y-axis 1207 if there is an adjacent window zone centerline. If there is not, we have reached the window's edge 1209 and need to check for existence of the top next right top of window column zone 1211. If there exists a zone just below, the logic thread will branch to obtain another image snap of this new zone 1205, and transfer the image to window grid or stitching memory. So if an adjacent zone center is below, move stem target zone center down to below adjacent zone center to align with the camera optic path centerline for a shot. If no zone center below or off window grid, move camera target zone center to adjacent right and top zone centerline center 1215. Otherwise we have taken and transferred all of the systematically scanned zone images and have a completed window zone sequence of images with stem origin window pixel unit grid in stitched memory 1213. If we have exceeded the window right edge zone, then we are also complete 1219. Otherwise move to right and top zone center on window grid and obtain an image or snap shot 1205, stitch sequence of image zones into memory using pixels offsets of zones from the origin. In an aspect of the invention, the logic to digitally control the optical path and the stem for position scans of small images and to digitally stitch a set of window zone micrograph images into a larger whole slide image will reside in the device.

In another embodiment, the optic stem is digitally controlled to rotate or extend out or retract the window pocket component, and the optical path is digitally controlled to extend or contract in distance from the stem center. This would allow many other digital stitching processes.

In another embodiment, images can be wirelessly transferred to AI analytics for identification or used for training data.

Therefore, while the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

What is claimed is:

1. An insitu bio-matter magnification device for AI analytics comprising:
    a housing having an optical and digital magnification path coupled to image detecting sensor and logic,
    a window pocket structurally coupled to a stem, window pocket component having an narrow enclosure for collecting bio sample,
    the window pocket providing photonic illumination source from a side of the collected sample opposite the image detecting sensor and directly into the optical and digital magnification path,
    the stem having at least one fiber optic channel for conducting selected pulsed or streamed frequency and wavelength light from single wavelength or tunable wavelength light sources into the window pocket,
    the window pocket component optically coupled an electro/optic channel stem distal end, for conducting selected frequency light from the housing to a window pocket side normal axis surface for illumination penetrating a specimen sample in the window pocket for optical imaging into an optical microscopy magnification path axis,
    an optical microscopy magnification path magnifying and focusing images on a digital CCD or CMOS detector,
    the image detector electronically coupled to electronic imaging logic for AI analytical processing and display of micrograph images,
    logic for digital control, image focus and image processing of images responsive to the stem and optical path positioning
    display of image processing results locally or wireless transfer to remote digital display device,
    whereby image comparisons and analytics can be accomplished and resulting digital image micrographs from optical window pocket collection programmatically processed, identified and verified in situ in real-time.

2. The insitu bio-matter magnification device for AI analytics as in claim 1 wherein the window pocket is an optical window pocket component forming a sample collecting enclosure coupled to an optical or electrical channel coupled stem coupled to a housing, the stem is rotatable and extendable-retractable under digital logic motor control.

3. The insitu bio-matter imaging AI analytics device as in claim 1 further comprising digital logic and optical component for programmatically selecting and controlling an intensity, frequency and power of light sources from which can be directed into insitu bio matter targets identified for the micrograph image processing.

4. The insitu bio-matter imaging AI analytics device as in claim 1 further comprising coupled local and wireless remote components for display of window pocket micrographs and identified images, displays from a set of displays consisting essentially of mobile, tablet, phablet, computer screen, and local tool small window.

5. The insitu bio-matter imaging AI analytics device as in claim 1 wherein the optical microscopy magnification path is selected from a group of microscopy optical paths including single lens, compound lens, confocal, TIRFM, Photonic, and Fluorescent.

6. The insitu bio-matter imaging AI analytics device as in claim 1 further comprising a coupled optical window properties transparent to selectable wavelength light from a group of light sources consisting essentially of visible, red, blue, UV-A, UV-B, UV-C, LED, excitation laser, fluorescent, full spectrum, multi-wave and Infra Red.

7. The insitu bio-matter imaging AI analytics device as in claim 1 further comprising a window pocket slide normal to the surface emitting light normal to the surface from a set of surface emitting light components consisting essentially of VCSEL, VXSEL, edge emitting laser diode, surface laser, internal mirror.

8. The insitu bio-matter imaging AI analytics device as in claim 1 further comprising a video capture and storage component for video in situ images for analytics processing.

9. The insitu bio-matter imaging AI analytics device as in claim 1 further comprising the housing distal end having internal cavity projected light sources from a set of light sources consisting essentially of laser, IR, UV and LED for accommodating disparate scattered light microscopy optical paths.

10. The insitu bio-matter imaging AI analytics device as in claim 1 further comprising a the optical microscopy magnification path for image capture in the window pocket.

11. The insitu bio-matter imaging AI analytics device as in claim 1 further comprising a local image library or remote wireless accessible database of bio micrographs and logic for image matching identification and Electronic Medical Record management.

12. The insitu bio-matter imaging AI analytics device as in claim 1 further comprising logic to digitally control the optical path and the stem for position scans of small images and to digitally stitch a set of window zone micrograph images into a larger whole slide.

13. A method for an insitu bio-matter magnification device for AI analytics comprising the steps of:
providing a housing with an optical and digital magnification path coupled to image detecting sensor and logic,
coupling a window pocket component structurally to a stem, window pocket component having an open enclosure for collecting bio matter sample to be magnified and imaged,
providing the window pocket with photonic source from a side of a collected sample illumination opposite the image detecting sensor and directly into an optical and digital magnification path,
providing the stem with at least one fiber optic channel for conducting selected pulsed or streamed frequency and wavelength light from single wavelength or tunable wavelength light sources into the window pocket,
optically coupling the window pocket component to an electro-optic channel stem distal end, stem conducting selected frequency light from the housing electro-optic source to a window pocket side normal axis surface for illumination penetrating a bio-matter sample in the window pocket for optical imaging into an optical microscopy magnification path axis,
providing an optical microscopy magnification path magnifying and focusing images on a digital image sensor,
electronically coupling the image sensor to electronic imaging logic for processing and display of magnified and focused images,
providing logic for digital control, image focus and AI analytics image processing of images responsive to the stem and optical path positioning, and
processing display of images locally or by wireless transfer to a remote digital display device,
whereby image comparisons and analytics can be accomplished and resulting digital image micrographs from optical window pocket collection programmatically processed, identified and verified in real-time.

14. The method for an insitu bio-matter magnification device for AI analytics as in claim 13 further comprising the steps of providing logic for programmatically selecting and controlling an intensity, frequency and power of light sources which can be directed into insitu bio matter targets identified for the micrograph image processing.

15. The method for an insitu bio-matter magnification device for AI analytics as in claim 13 further comprising the steps of coupling local and wireless remote components for display of window pocket micrographs and identified matching images, displays from a set of displays consisting essentially of mobile, tablet, phablet, computer screen, and local tool small window.

16. The method for an insitu bio-matter magnification device for AI analytics as in claim 13 further comprising the steps of providing an optical microscopy magnification path selected from a group of microscopy optical paths including single lens, compound lens, confocal, TIRFM, Photonic, and Fluorescent.

17. The method for an insitu bio-matter magnification device for AI analytics as in claim 13 further comprising the steps of coupling optical window transparent to selectable wavelength light from a group of light sources consisting essentially of visible, red, blue, UV-A, UV-B, UV-C, LED, excitation laser, fluorescent, full spectrum, multi-wave and Infra Red.

18. The method for an insitu bio-matter magnification device for AI analytics as in claim 13 further comprising the steps of providing local image library or remote wireless accessible database of bio micrographs and logic for image matching or identification and Electronic Medical Record management.

19. The method for an insitu bio-matter magnification device for AI analytics as in claim 13 further comprising the steps of providing logic to digitally control the optical path and the stem for position scans of small images and to digitally stitch a set of window zone micrograph images into a larger whole slide.

20. The method for an insitu bio-matter magnification device for AI analytics as in claim 13 wherein the window pocket is an optical component forming a sample collecting enclosure coupled to an optical or electrical channel coupled to a housing, the stem is rotatable and extendable-retractable under digital logic control.

* * * * *